United States Patent
Block et al.

(10) Patent No.: US 8,658,833 B2
(45) Date of Patent: Feb. 25, 2014

(54) GARLIC PROCESSING

(75) Inventors: Eric Block, Niskayuna, NY (US);
Murree Groom, Thetford (GB)

(73) Assignee: Ecospray Limited (GB)

(*) Notice: Subject to any disclaimer, the term of this patent is extended or adjusted under 35 U.S.C. 154(b) by 1033 days.

(21) Appl. No.: 12/514,171

(22) PCT Filed: Nov. 9, 2007

(86) PCT No.: PCT/GB2007/004279
§ 371 (c)(1),
(2), (4) Date: May 8, 2009

(87) PCT Pub. No.: WO2008/059213
PCT Pub. Date: May 22, 2008

(65) Prior Publication Data
US 2010/0069674 A1 Mar. 18, 2010

(30) Foreign Application Priority Data

Nov. 11, 2006 (GB) ................................. 0622549.4
Jun. 12, 2007 (GB) ................................. 0711308.7

(51) Int. Cl.
*C07C 319/24* (2006.01)
*C07C 321/20* (2006.01)

(52) U.S. Cl.
USPC .................. 568/18; 568/21; 568/22; 568/27; 564/500

(58) Field of Classification Search
None
See application file for complete search history.

(56) References Cited

U.S. PATENT DOCUMENTS

| | | | |
|---|---|---|---|
| 4,551,259 A | 11/1985 | Braid | |
| 5,149,879 A * | 9/1992 | Awazu et al. | 568/21 |
| 2008/0194666 A1* | 8/2008 | Jabbour et al. | 514/408 |
| 2009/0317500 A1* | 12/2009 | Sadler-Bridge et al. | 424/754 |

FOREIGN PATENT DOCUMENTS

WO 2006/109028 A 10/2006

OTHER PUBLICATIONS

Toohey, J. "Sulphane sulphur in biological systems: a possible regulatory role," Biochem. J. (1989) 264: 625-632.*
Hofle, G. et al., "Thiosulfoxides. The intermediates in rearrangement and reduction of allylic disulfides," JACS (1971) 93: 6307-6308.*
Kim, J. et al. "Antimicrobial activity of alk(en)yl sulfides found in essential oils of garlic and onion," Food Sci. Biotechnol. (2004) 13: 235-239.*
N. Yamada, et al.: "Direct preparation of anhydrous sodium oligo sulphides from metal sodium and elemental sulphur in aprotic media directed toward synthesis of silane coupling agent", Chemistry Society of Japan, Chemistry Letters No. 4, Apr. 2002, pp. 454-455, ISSN: 0366-7022, figure 2, $4^{th}$ entry.
K.C. Agarwal: "Therapeutic actions of garlic constituents", Medical Research Reviews, vol. 16, No. 1, Jan. 1996, pp. 111-124, Wiley, Hoboken, NJ, US, ISSN: 0198-6325, pp. 111-112.
R.C. Fuson et al.: ":Levinstein mustard gas. IV. The bis-(2-chloroethyl) polysulphides", Journal of Organic Chemistry, vol. 11, No. 5, Sep. 1946, pp. 487-498, American Chemical Society, Washington, DC, US, ISSN: 0022-3263, p. 493, last paragraph.
Münchberg et al., "Polysulfides as biologically active ingredients of garlic", Mar. 14, 2007, pp. 1505-1518.

* cited by examiner

*Primary Examiner* — Johann R Richter
*Assistant Examiner* — Mark Luderer
(74) *Attorney, Agent, or Firm* — Cantor Colburn LLP

(57) ABSTRACT

A method of producing polysulfides comprising the step of adding elemental sulphur to an allicin-containing plant extract. In preferred embodiments, the plant extract is mechanically treated members of the genus *Allium*, especially garlic. In further preferred aspects of the invention, the plant extract and sulphur mixture is heated, and the pH is controlled to allow manipulation of the polysulfide chain length. The addition of organic bases, containing nitrogen lone pairs, allows further control of polysulfide chain length.

12 Claims, No Drawings

GARLIC PROCESSING

This application is a national phase of International Application No. PCT/GB2007/004279 filed Nov. 9, 2007 and published in the English language.

FIELD OF THE INVENTION

The invention relates to methods of processing extracts from the genus *Allium*, especially garlic, to manipulate the concentration and spectrum of polysulfides contained therein. The invention also relates to the products so produced, and their industrial uses, especially as crop protection agents and therapeutic preparations.

BACKGROUND AND PRIOR ART KNOWN TO THE APPLICANT

Plants of the genus *Allium* and in particular, garlic, have evolved to use various sulphur-containing molecules as agents of defence against tissue damage from microbes and feeding damage from herbivores.

The garlic plant's primary means of chemical defence requires conversion of alliin, a sulphur-containing constituent of the plant by an allinase enzyme. The result of this interaction is release of allicin, an unstable and biologically active molecule containing two sulphur molecules. Allicin in turn converts to more reduced forms of sulphur, such as polysulfides with either methyl or allyl functional groups attached to either end of the sulphur chain.

Molecules with shorter sulphur chain lengths such as diallyl disulfide, dimethyl disulfide and dimethyl sulfide are quite stable, with limited water solubility and can be produced in very high purity by synthetic means. A vast body of literature has identified a range of biological effects from these short sulphur chain length molecules, including repellency, insecticidal effects, physiological effects on plants, stimulatory effects on fungal spore germination and possibly a wide range of therapeutic effects in man, including antibiotic and anti cancer properties.

Polysulfide molecules with higher sulphur chain lengths ($S=>3$, i.e. containing three or more sulphur atoms) are also very active with increasing evidence of a very wide range of biological activity (insecticidal, nematicidal, mollusicidal, repellent, anti cancer, antibiotic and fungicidal). Numerous groups are starting to examine the biochemistry of the higher chain length polysulfides in great detail with particular emphasis on sites of action for diallyl trisulfide and diallyl tetrasulfide. A recent review of the known and potential activity of polysulfides outlines the area: Münchberg, U. et al, "*Polysulfides as biologically active ingredients of garlic*", Org. Biomol. Chem., 2007, 5, 1505-1518.

A consensus is emerging that the polysulfides derived from garlic offer a new group of actives for major new therapeutic products against many forms of human cancer. A similar view on the potential of these molecules as crop protection agents is also rapidly emerging.

Whilst it is possible to chemically synthesize polysulfides ab initio, considerable advantages flow from using polysulfides derived from the parent plant material (e.g. in a garlic extract). Firstly, the use of the compounds within the plant-derived matrix confers some stability to the spectrum of polysulfides. Furthermore, the chemical synthesis of these compounds is complex, and involves handling significantly hazardous materials. The plant-derived material imposes a significantly lower burden on any manufacturing environment, and on the environment generally. There is a need, therefore, for technologies to aid the manipulation, control and optimisation of methodologies for processing garlic and other *Allium*-derived extracts, and indeed any allicin-containing plant extract such as extracts derived from garlic, onions, leeks, chives, shallots or cabbage. It is among the objects of the present invention to attempt a solution to some of these problems.

SUMMARY OF THE INVENTION

Accordingly, the invention provides, in a first broad aspect, a method of producing polysulfides comprising the step of adding elemental sulphur to an allicin-containing plant extract.

In most plants, allicin (2-propene-1-sulfinothioic acid S-2-propenyl ester) is produced by the action of the enzyme alliinase (S-alk(en)yl-L-cysteine sulfoxide lyase) on the substrate alliin ((2R)-2-amino-3-[(R)-prop-2-enylsulfinyl]propanoic acid). The alliin and alliinase are present in the plant in separate compartments, the enzymatic conversion only occurring following damage to the plant tissue. The term "extract" therefore includes processed plant material that has been mechanically treated to effect this transformation. Appropriate mechanical treatments would include cutting, crushing or mincing the plant material. A particularly preferred method is the use of a liquidisation process using a commercial "blender" to effect a very fine particle size reduction. The extract may be subject also to a water-removal stage to improve stability of the product (see e.g. PCT/GB2006/001290).

In particularly preferred embodiments, the elemental sulphur comprises amorphous, powdered sulphur ("Flowers of Sulphur"). It is envisaged, however, that other allotropes of sulphur, or molten sulphur could also be employed.

Preferably, and in a second aspect, the said plant extract is an extract of the genus *Allium*, and especially an extract of garlic, *Allium sativum* L.

In any method, and in a third aspect, it is particularly preferred that the method further comprises the step of heating the mixture so produced; preferably, in a fourth aspect, the said mixture is heated to at least 60 degrees Celsius, and more preferably, in a fifth aspect, the said mixture is heated to at least 70 degrees Celsius.

In any method, it is particularly preferred, in a sixth aspect, that the sulphur is added to a concentration of at least 0.1% (w/w), more preferably to a concentration of at least 0.2% (w/w), even more preferably to a concentration of at least 0.5% (w/w); and most preferably, in a seventh aspect, wherein sulphur it added to a concentration of at least 1% (w/w).

The invention also provides a method of producing polysulfides of increased chain length comprising a method as recited above, and characterised in that the pH of the mixture so produced is adjusted to be below pH 4.0. It is particularly preferred that such pH adjustment is carried out with an organic acid such as citric acid, acetic acid or lactic acid. Mineral acids such as hydrochloric acid and especially sulphuric acid are also preferred.

The invention also provides a method of producing polysulfides of decreased chain length comprising a method according to a method of the first to the seventh aspects, and characterised by the addition of an amine. Compounds possessing nitrogen atoms with lone pair electrons are particularly preferred, and especially dibutyl amine, or an amino acid. Amino acids having additional nitrogen atoms on side chains are especially preferred. Preferably, such a method is further characterised in that the pH of the mixture so produced is adjusted to be above pH 8.

Included within the scope of the invention is a method of producing polysulfides substantially as described herein.

Also included within the scope of the invention is a crop protection agent produced according to any method described herein.

Also included within the scope of the invention is a pharmaceutical or therapeutic composition produced according to any method described herein.

DESCRIPTION OF PREFERRED EMBODIMENTS

As illustrations of various embodiments of the invention, examples of methods of manipulating the polysulfide composition of garlic extracts will be described:

Phase 1 Experiments

Samples of allicin-enriched garlic extract ("standard solution") were obtained from Neem Biotech Ltd, Cardiff, CF14 6HR, United Kingdom. The allicin concentration in the sample material was around 10,000 ppm (w/w).

Such allicin-enriched samples were used for analytical simplicity, but the examples described below, and the methods described herein may equally be used with non-enriched allicin-containing plant extracts. Suitable starting material may be produced by the mechanical treatment of bulbs of the genus *Allium*, and especially from garlic, *Allium sativum* L.

Two sub-samples of the allicin-enriched material were used, one of which was used in studies at 60° C. and one used in studies at 70° C.

At each temperature the following reaction conditions were generated and maintained for one hour:—
(1) Standard solution (5 g) heated.
(2) Standard solution (5 g) with 50 mg of added elemental sulphur, then heated
(3) Standard solution (5 g) with 5 mg of added elemental sulphur, then heated.
(4) Standard solution (5 g) with 5 mg of added elemental sulphur and 20 mg of dibutyl amine, then heated.

The sulphur used was in the form of commercial, powdered sulphur ("Flowers of Sulphur").

Both temperature studies were controlled against a sample maintained in a refrigerator for the same one-hour period that the test solutions were being heated.

Following completion of the heating phase, the solutions were rapidly cooled and then analysed by HPLC a few hours later.

Table 1 details the concentration of polysulfides found in the control samples (refrigerated for 1 hour).

TABLE 1

| Molecule | Control to 60 degree sample group | | Control to 70 degree sample group | |
|---|---|---|---|---|
| | Actual concentration mAUs* | % of polysulfide chromatogram | Actual concentration mAUs* | % of polysulfide chromatogram |
| DAS | 0 | 0 | 0 | 0 |
| DAS2 | 17.3 | 11.6 | 100 | 4.6 |
| DAS3 | 66.7 | 44.7 | 1311.1 | 61.3 |
| DAS4 | 12.7 | 8.5 | 128.6 | 6.0 |
| DAS5 | 0 | 0 | 14.5 | 0.7 |
| DAS6 | 0 | 0 | 0 | 0 |

*Area under HPLC peak: milli-Absorbance Units · s
The molecules analysed were as follows:
DAS: Diallyl sulfide
DAS2: Diallyl disulfide
DAS3: Diallyl trisulfide
DAS4: Diallyl tetrasulfide
DAS5: Diallyl pentasulfide
DAS6: Diallyl hexasulfide Reaction condition (1): This sample was heated to either 60° C. or 70° C., and held at that temperature for 1 hour. The results of analysis of products results from this treatment are presented in Table 2 (nomenclature as before):

TABLE 2

| Molecule | 60 degree heating | | 70 degree heating | |
|---|---|---|---|---|
| | Actual concentration mAUs | % of polysulfide chromatogram | Actual concentration mAUs | % of polysulfide chromatogram |
| DAS | 0 | 0 | 0 | 0 |
| DAS2 | 20 | 15.6 | 78.5 | 6.2 |
| DAS3 | 79.0 | 60.9 | 820 | 64.7 |
| DAS4 | 13.0 | 10.0 | 118.4 | 9.3 |
| DAS5 | 0 | 0 | 12.6 | 1.0 |
| DAS6 | 0 | 0 | 0 | 0 |

Reaction condition (2): This sample was treated by the addition of 50 mg elemental sulphur to the 5 g of sample, giving a total concentration of 1% (w/w). The sample was mixed by vigorous shaking, and held at either 60° C. or 70° C. The results of analysis of products results from this treatment are presented in Table 3 (nomenclature as before):

TABLE 3

| Molecule | 60 degree sample group | | 70 degree sample group | |
|---|---|---|---|---|
| | Actual concentration mAUs | % of polysulfide chromatogram | Actual concentration mAUs | % of polysulfide chromatogram |
| DAS | 0 | 0 | 0 | 0 |
| DAS2 | 26.4 | 13.0 | 28.2 | 3.3 |
| DAS3 | 99.5 | 48.7 | 347.6 | 41.1 |
| DAS4 | 23.6 | 11.5 | 241.8 | 28.64 |
| DAS5 | 18.0 | 8.8 | 102.8 | 12.2 |
| DAS6 | 9.1 | 4.4 | 20.7 | 2.4 |

Reaction condition (3): This sample was treated by the addition of 5 mg elemental sulphur to the 5 g of sample, giving a total concentration of 0.1% (w/w). The sample was mixed by vigorous shaking, and held at either 60° C. or 70° C. The results of analysis of products results from this treatment are presented in Table 4 (nomenclature as before):

TABLE 4

| Molecule | 60 degree sample group | | 70 degree sample group | |
|---|---|---|---|---|
| | Actual concentration mAUs | % of polysulfide chromatogram | Actual concentration mAUs | % of polysulfide chromatogram |
| DAS | 0 | 0 | 0 | 0 |
| DAS2 | 27.3 | 14.5 | 133.8 | 6.2 |
| DAS3 | 104.8 | 55.76 | 1195.7 | 55.4 |
| DAS4 | 19.8 | 10.5 | 313 | 14.5 |
| DAS5 | 6.2 | 3.3 | 88.5 | 4.1 |
| DAS6 | 0 | 0 | 0 | 0 |

Reaction condition (4): This sample was treated by the addition of 5 mg elemental sulphur to the 5 g of sample, giving a total concentration of 0.1% (w/w) sulphur and also by the addition of 20 mg dibutyl amine (giving a concentration of 0.4% w/v). The sample was mixed by vigorous shaking, and held at either 60° C. or 70° C. The results of analysis of products results from this treatment are presented in Table 5 (nomenclature as before):

TABLE 5

| Molecule | 60 degree sample group | | 70 degree sample group | |
|---|---|---|---|---|
| | Actual concentration mAUs | % of polysulfide chromatogram | Actual concentration mAUs | % of polysulfide chromatogram |
| DAS | 7.2 | 4.1 | 3.0 | 0.5 |
| DAS2 | 21.5 | 12.0 | 44.7 | 7.1 |
| DAS3 | 84.2 | 47.1 | 379.0 | 60.4 |
| DAS4 | 37.3 | 20.9 | 88.7 | 14.1 |
| DAS5 | 12.1 | 6.8 | 29.7 | 4.7 |
| DAS6 | 0 | 0 | 0 | 0 |

Although there were quite substantial differences in the initial polysulfide concentrations in the two 'allicin-enriched' samples, the data show a clear consistency in reactivity in both solutions to the addition of heat, sulphur and base amines.

The initial data shown in tables 1-5 clearly show that the pattern of conversion of the allicin to polysulfides in the absence of sulphur was very similar at the two temperatures, with no indication that the higher polysulfides such as DAS4, DAS5 and DAS6 increased in concentration as incubation temperature increased.

When sulphur was added at 50 mg/5 g (1% w/w), there was a clear increase in the concentration of the higher polysulfides at both temperatures. The concentration of DAS4 doubled at both temperatures. The concentration of DAS5 increased five-fold at 70° C. and DAS6 appeared for the first time at both 60 and 70° C.

At the lower level of sulphur addition, 5 mg/5 g (0.1% w/w), there was a similar gain in the higher polysulfides to that seen at the 50 mg addition, but most importantly, there was an even greater relative gain in DAS4 at 70° C., which appeared to be compensated for by a reduction in the relative concentrations of DAS5 and DAS6. DAS4 is a particularly important polysulfide in relation to crop protection.

These results clearly show that based on DAS4 concentration, there is considerable scope to enhance garlic extracts to increase the concentration of DAS4 through a combination of sulphur addition and mild heating.

On first analysis sulphur addition at 0.1% w/w (ca.1 kg/tonne) could triple DAS4 concentration if allicin-enriched solutions are subsequently heated to 70° C. for one hour.

The last experimental combination included the addition of dibutyl amine with 5 mg of sulphur, which produced a completely different pattern of polysulfide accumulation to just sulphur only addition. The addition of the amine catalysed the decomposition of the higher polysulfides and produced two outcomes related to the incubation temperature: At the colder temperature the catalysis of dibutyl amine in the presence of 0.1% w/w sulfur appeared to triple DAS4 concentration when compared to the cold incubation control. This contrasted with a substantial reduction of DAS4 concentration observed at the 70° C. incubation temperature. In addition dibutyl amine (nitrogen lone pair of electrons) also catalysed the generation of diallyl sulfide DAS, the first time that this molecule appeared in any of the reaction sequence.

This group of experiments clearly identifies considerable scope for enhancements in the production of polysulfide-containing compositions obtainable from plant sources such as garlic. These enhancements could have significant cost and effectiveness results.

Phase 2 Experiments

In a further series of experiments, manipulation of the polysulfide composition of garlic extracts was carried out on freshly-prepared extracts, and also extracts that had been stored in a frozen state for approximately three months, to demonstrate the applicability of the technique on samples having variation in their background matrix, that might be a result from typical biological variation often observed with such natural products. The samples had different appearances (a different colour) this being indicative of differences between the plant-derived matrix in which the allicin is found.

The samples, again sourced from Neem Biotech Ltd, containing approximately 10,000 ppm of allicin were stored in a frozen state. Sub-samples were defrosted and weighed in to 10 g aliquots followed by various amendments with elemental sulphur.

All samples were then heated at 70° C. for 1 hour with periodic vigorous shaking, prior to rapid cooling in iced water.

After cooling, 100 mg samples of the reacted supernatants were added to 10 ml of pure ethanol, the resulting solutions were then mixed and sub-samples filtered prior to analysis by HPLC.

The samples were coded as "Nov 06" for the aged samples, which was a light orange in colour. The un-aged sample was coded as "Mar 07", and was distinctly green in colour; both had a similar smell of freshly-crushed garlic.

The reactions with sulphur were controlled against a sub-sample heated with no sulphur addition and a sub-sample with no sulphur addition placed in a refrigerator. After one hour all experimental solutions were processed and analysed by HPLC as a group.

The following results were obtained:

TABLE 6

| | Sample: | | | | | | | |
|---|---|---|---|---|---|---|---|---|
| Molecule | November 2006 Cold | March 2007 Cold | November 2006 Heat | March 2007 Heat | November 2006 Heat + 20 mg Sulphur | March 2007 Heat + 20 mg Sulphur | November 2006 Heat + 50 mg Sulphur | March 2007 Heat + 50 mg Sulphur |
| DAS | — | — | — | — | — | — | — | — |
| DAS2 | — | 9.85 | — | — | — | — | 7.56 | — |
| DAS3 | 39.27 | 61.06 | 136.46 | 121.85 | 86.89 | 85.6 | 116.29 | 106.9 |
| DAS4 | 6.4 | 9.64 | 23.01 | 20.01 | 22.23 | 21.89 | 28.24 | 34.38 |
| DAS5 | — | — | — | — | 14.58 | 15.69 | 18.80 | 38.35 |
| DAS6 | — | — | — | — | — | — | 15.18 | 34.07 |
| DAS7 | — | — | — | — | 32.73* | 35.85* | 94.93* | 288.17* |

*These responses might also include a response from elemental sulphur, and so should be treated with caution. Units for all results are mAUs.

Nomenclature for DAS, DAS2 etc is as above. DAS7 is diallyl heptasulfide.

The data clearly show that some polysulfides were present in the samples at the outset, with both samples having a degree of similarity at the initiation of the experiment. The impact of heat is clear, with both samples, Nov06 and Mar07 showing a clear increase in DAS3 and DAS4 concentrations. The Nov06 samples show the greatest relative gain: 247% against 99% for the Mar07 samples. A similar pattern is also apparent for the gain in DAS4 (259% vs 107%).

The inclusion of sulphur at 20 mg/test cell, clearly induces the appearance of DAS5 at what appears to be the expense of DAS3. DAS7 also appears, but this is yet to be confirmed due to the possibility of co-elution of DAS7 and elemental sulphur.

Adding sulphur to 50 mg/test cell appears to produce a generalised increase in all polysulfides beyond DAS3, with the appearance of DAS2 in the Nov06 samples and DAS6 in both the Nov06 and Mar07 samples.

The data in general appears to confirm that the different sources of allicin-enriched material exhibit differing reactivity to heat, with the Nov06 sample converting relatively more of the allicin to DAS3 and DAS4. In contrast to this the Mar07 sample appears to convert more of the elemental sulphur to the higher polysulfides (DAS5 and DAS6) in what appears to be a reaction involving DAS3, since this molecule is clearly diminishing in concentration as the higher polysulfides increase.

These data, together with other studies on the Nov06 samples (as described above) provide strong evidence that the condition of the carrier matrix affects the allicin to polysulfides conversion process either through heat only, or with heat and additional sulfur.

Both the phase 1 and phase 2 studies show that elevation in sulphur concentration leads to DAS6 appearance. The two studies also show that an intermediate level of sulphur addition leads to generation of DAS5, without the appearance of DAS6.

DAS4 also is shown to increase in concentration with increasing sulphur addition, with up to fourfold increases in concentration noted in both the Nov06 and Mar07 samples when sulphur was added at 50 mg/10 g ratios.

Irrespective of the relative differences in 'reactivity' of the two-allicin sources, there is a clear general outcome to the combination of heat and sulphur addition.

Heat converts allicin to DAS3, increasing sulphur converts DAS3 to DAS4, DAS5 and DAS6, the relative gains of which appear to be affected by the matrix and sulphur concentration. The first experiment on the Nov06 material (phase one) also clearly showed that introduction of a base (e.g. dibutyl amine) had a catalytic effect on decomposition of the higher polysulfides, in particular diallyl tetrasulfide and diallylpentasulfide causing the appearance of diallylsulfide.

General Observations

The phase one and phase two experiments, above, indicate a high degree of general predictability in the conversion of allicin to polysulfides. Heat, in combination with increasing sulphur inevitably leads to accumulation of the higher polysulfides DAS3, DAS4, DAS5 and DAS6.

The end points in the conversion process are susceptible to relative sulphur concentration, suggesting that the concentration relationship of DAS3, DAS4, DAS5 and DAS6 can be manipulated by alterations in the process control.

There is also some evidence from the phase one study that the pH of the matrix (and hence the state of protonation of the nitrogen lone pairs in e.g. endogenous and added amines) has a profound effect on the accumulation of, for example DAS4 and DAS5.

There appears therefore to be two opposing effects that operate in a 'typical' garlic juice extract loaded with allicin. One effect is the predictable build up and accumulation of higher polysulfides as a result of addition of elemental sulphur and heat. The second effect is the rapid catalytic breakdown of these higher polysulfides to DAS and DAS2 in the presence of unprotonated amines. These two effects therefore enable the skilled addressee to manipulate the spectrum of polysulfides to produce a desired product.

With appropriate manipulation of the matrix prior to work up, for example pH control and regulation of amino acid content, conditions for substantial generation of DAS4, DAS5 and DAS6 can be generated prior to heating and sulphur addition. Manipulation of the interrelationship between heat and sulphur enables quite substantial differentiation in the actual and relative concentrations of DAS3, DAS4, DAS5 and DAS6 to be factored in to the manufacturing process.

The invention claimed is:

1. A method of producing polysulfides comprising the step of adding elemental sulphur to an allicin-containing plant extract.

2. The method of claim 1 wherein the said plant extract is an extract of the genus *Allium*.

3. A method according to claim 1 further comprising the step of heating the mixture so produced.

4. A method according to claim 3 wherein the said mixture is heated to at least 60 degrees Celsius.

5. A method according to claim 3 wherein the said mixture is heated to at least 70 degrees Celsius.

6. A method according to claim 1 wherein sulphur is added to a concentration of at least 0.1% (w/w).

7. A method according to claim 1 wherein sulphur is added to a concentration of at least 1% (w/w).

8. A method of producing polysulfides of increased chain length comprising a method according to claim 1, wherein the pH of a mixture so produced is adjusted to be below pH 4.0.

9. A method of producing polysulfides of decreased chain length comprising a method according to claim 1, further including an amine.

10. A method according to claim 9 wherein the said amine is dibutyl amine.

11. A method according to claim 9 wherein the said amine is an amino acid.

12. A method according to claim 1, wherein the pH of a mixture so produced is adjusted to be above pH 8.

* * * * *